United States Patent [19]
Pauly

[11] Patent Number: 5,876,729
[45] Date of Patent: Mar. 2, 1999

[54] USE OF EXTRACTS OF TAMARIND SEEDS RICH IN XYLOGLYCANS AND COSMETIC OR PHARMACEUTICAL PRODUCT CONTAINING SUCH EXTRACTS

[75] Inventor: Gilles Pauly, Pulnoy, France

[73] Assignee: Laboratoires Serobiologiques (SA), Pulnoy, France

[21] Appl. No.: 582,583

[22] Filed: Jan. 3, 1996

[30] Foreign Application Priority Data

Jan. 3, 1995 [FR] France ................................. 95 00078

[51] Int. Cl.⁶ .............................. A01N 65/00; A61K 7/00; A61K 7/48; A61K 31/715
[52] U.S. Cl. ................................. 424/195.1; 424/197.1; 514/783; 514/773; 514/777
[58] Field of Search ............................. 424/195.1, 197.1; 514/773, 777, 783

[56] References Cited

FOREIGN PATENT DOCUMENTS 9 112 922  6/1994  Japan .
7 053 335  2/1995  Japan .

*Primary Examiner*—Michael P. Woodward
*Assistant Examiner*—Mary K. Zeman
*Attorney, Agent, or Firm*—Young & Thompson

[57] ABSTRACT

The use of extracts of tamarind seeds enriched in xyloglycans as an active agent in a cosmetic and/or pharmaceutical product for topical usage for the skin and/or other exposed parts of the body. The extracts of tamarind seeds enriched in xyloglycans are present in the cosmetic and/or pharmaceutical product for topical use in a total weight fraction comprised between 0.05% and 100%, preferably between 1% and 25% by weight.

8 Claims, No Drawings

USE OF EXTRACTS OF TAMARIND SEEDS RICH IN XYLOGLYCANS AND COSMETIC OR PHARMACEUTICAL PRODUCT CONTAINING SUCH EXTRACTS

The present invention relates to the use of extracts of tamarind seeds rich in xyloglycans in cosmetic and/or pharmaceutical applications.

The tamarind tree is a large evergreen tree belonging to the Leguminous family and whose fruits are large dehiscent pods, with a pulpy mesocarp, each of which encloses 4 to 12 seeds.

It is already known to use in various ways the pulp of the pods and the seeds of these latter.

Thus, the pulp of the fruit, rich in free and salified organic acids and containing a large quantity of simple sugars, is used in foodstuffs (sauces, beverages) and as a mild laxative.

The pulp or flesh of the seeds itself contains principally polysaccharides, but also proteins, lipids and mineral materials.

Said polysaccharides are principally xyloglycanic biopolymers or xyloglycans whose composition is generally as follows:

| | |
|---|---|
| Xylose | about 18% |
| Galactose | about 23% |
| Glucose | about 55% |
| Arabinose | about 4% |

It is already known to use the powder obtained from the seeds as sizing for textile fibers, as thickening agent, as coating or surfacing agent in the paper industry, the cardboard industry and in the textile industry.

Similarly, the polysaccharides extracted from said tamarind seeds are known, in addition to the above uses, to produce gels in the presence of sugars, over a wide pH range.

Thus, said polysaccharides are used as fruit pectin substitutes in the production of jams, jellies and marmalades and as stabilizers for ice cream and mayonnaise.

Moreover, the use of specific isolated polysaccharides, such as hyaluronic acid, chitine, cellulose, carraghenates, algal polysaccharides and the like, is known in cosmetology, because of their softening, hydrating, protective and film-forming properties.

However, the inventors of the present invention have discovered that, in an unexpected and surprising manner, the xyloglycans extracted from tamarind seeds have, because of their particular composition, on the one hand, immediate properties more varied and quantitatively substantially more important than those of the mentioned known polysaccharides, on the other hand, long term supplemental effects and finally, very high tolerance.

Thus, the principal object of the present invention concerns the use or application of tamarind seed extracts rich in xyloglycans as active agents in a cosmetic and/or pharmaceutical product or preparation for topical use for the skin and/or the other exposed body parts.

These tamarind seed extracts rich in xyloglycans can be obtained by conventional extraction techniques for polysaccharides, such as hot extraction in aqueous, hydroalcoholic or alcoholic solutions, in acid or neutral media, on defatted powders or not.

One could proceed, for example, by carrying out the following operations: extraction of the kernel from the tamarind seeds (after decortication and elimination of the envelope) and crushing of these latter, treatment of said seed powder with a solvent adapted to eliminate lipids, extraction of the xyloglycans from the seed powder by dispersion of this latter in an aqueous acid solution, elimination of the insoluble fraction from the solution of xyloglycans, recovery of the supernatant solution rich in xyloglycans, adjustment as needed of the pH, and finally, eventual subjection of said solution enriched in xyloglycans to at least one complementary treatment so as to modify the presentation, the form and/or the composition of said extracted xyloglycans, before use of said xyloglycans or said extract rich in xyloglycans as an active agent to produce cosmetics and/or pharmaceuticals for topical usage (dermopharmaceutical) for the skin and/or other exposed body parts.

The solvent used to eliminate the lipids from the seed powder is preferably hexane (non-limiting example).

Moreover, the aqueous acid solution used for extraction consists preferably of an aqueous solution of an organic acid, such as for example citric acid, tartaric acid or malic acid, diluted to between 0.01% and 10%, preferably to 0.2%, the extraction of the xyloglycans being carried out with vigorous heating and agitation.

For the extraction of the xyloglycans, the powder or flour of tamarind seeds is preferably dispersed in a quantity of extractive solvent 20 to 40 times greater in weight than said powder or flour and the temperature of the solution in the course of extraction is maintained at a value comprised between 20° C. and 140° C., preferably between 80° C. and 100° C.

The duration of the extraction phase of the xyloglycans is, under the conditions of temperature and agitation indicated above, variable between 30 minutes and several hours. However, most of the extraction is generally achieved by the end of 40 minutes.

During this extraction phase, the insoluble fraction of the powder or flour is separated from the liquid extract containing the xyloglycans, by centrifugation, screening or the like.

Moreover, the fraction of solution rich in xyloglycans can, after selective removal of the liquid extract containing the xyloglycans, be adjusted to a pH value suitable for its ultimate use.

The complementary treatment can comprise dehydration of the solution enriched in xyloglycans by lyophilization or atomization or direct extraction and selective purification of the xyloglycans from said enriched solution, by precipitation by an organic solvent followed by elimination of the solvent and drying.

The organic solvent used for precipitation can preferably consist in ethyl alcohol mixed in the solution enriched in xyloglycans with a volume ratio of 1. The fibrous precipitate, from said precipitation, is then recovered for example by filtration or screening and subjected to pressing to eliminate as much as possible of the imbibed solvent, before proceeding with its drying.

The incorporation of tamarind grain extracts rich in xyloglycans in cosmetic and/or pharmaceutical products or preparations for cutaneous or capillary use or the like can be effected in the form of an aqueous solution or suspension, a hydropolyolic suspension or even a dehydrated condition, after re-dissolution effected at the time needed, the incorporation preferably taking place after re-dissolution in a suitable solvent or integration into a formulation permitting the utilization of the specific properties of the xyloglycans.

However, in most of the complementary treatments provided above or in variations of these latter, there can also be provided other treatments of the solution rich in xyloglycans or extracts enriched in xyloglycans in solid form, comprising operations of modification of the form and/or composition of the extracted xyloglycans, such as for example partial or total hydrolysis, polymerization, cross-linking with aldehydes, condensation grafting with fatty acids, methylation or vectorization, for example by encapsulation in the form of microspheres or microcapsules, liposomes, nanocapsules, nanospheres, microsponges, clathrates or the like.

According to the invention, the tamarind seed extracts enriched in xyloglycans are present in the cosmetic and/or pharmaceutical product for topical use according to a total weight fraction comprised between 0.05% and 100%, preferably a total weight fraction comprised between 1% and 25%.

These products containing extracts enriched in xyloglycans generally comprise between 3% and 10% of pure xyloglycans, preferably about 5%. However, these products could also have particularly a concentration of xyloglycans substantially higher and, in the extreme case, be constituted of practically pure xyloglycans.

The present invention also has for its object a cosmetic and/or pharmaceutical preparation or product for topical use for the skin and/or the other exposed parts of the body, comprising between 0.05% and 100% by weight of extracts of tamarind seeds enriched in xyloglycans.

Preferably, the said preparation or product can consist of a treatment composition comprising between 1% and 25% by weight of extracts of tamarind seeds enriched in xyloglycans, these latter having a fractional constituent composition identical to that existing in the kernels of tamarind seeds in their natural condition.

The object of the present invention can be carried out more generally in any cosmetic and/or dermopharmaceutical base suitable for application to the skin or other exposed parts of the body, and compatible with the activity of the xyloglycans.

During use of a cosmetic and/or pharmaceutical product for topical use according to the invention and adapted for a cutaneous use, there is experienced immediately a softening and velvety sensation, improved cutaneous comfort as well as the appearance of a satiny look, particularly during application to sensitive or dry skin.

These effects result directly from the film forming, softening, smoothing, hydrating and reparative properties, that act immediately, of the xyloglycans extracted from tamarind seeds.

There is thus an immediate improvement in the tactile qualities of the skin as mentioned above, thanks to the formation on the surface of a strongly hydrated macromolecular network, whose character is hydrating, elastifying and viscoelastic.

Moreover, there is also observed a protective and conditioning effect, which is quite substantial, without a blocking effect.

Furthermore, in addition to the mentioned immediate effects, the cosmetic products for cutaneous application according to the invention also have long-term activities of an immunomodulatory and immunostimulatory nature.

As a result, the xyloglycans extracted from tamarind seeds have a particular application on the one hand, in the framework of products for skin care such as anti-aging products, aftershave products, sunscreen and after-sun products, and, on the other hand, in the field of makeup products such as tinted creams, makeup base, lipsticks and the like.

However, according to a modified use, the present invention relates also to cosmetic products in the field of capillary treatment, such as shampoos, balms or lotions, and the integration of the xyloglycans extracted from tamarind seeds in these products permits rendering the hair softer, smoother and easier to arrange, because particularly of the film-forming effect that is obtained.

By way of non-limiting examples of practical embodiments of the invention, there will be described hereafter different cosmetic or pharmaceutical products or preparations for topical use for the skin or other exposed parts of the body, comprising extracts of tamarind seeds, enriched in xyloglycans.

EXAMPLE 1

A cosmetic product in the form of a face cream according to the invention can for example have a weight composition constituted from fractions A, B and C as follows, as indicated hereinafter.

| Fraction A: | |
| --- | --- |
| Cetostearyl alcohol (and) ceteareth-20 | 5.00% |
| Glycerol stearate (and) stearate of PEG-100 | 3.50% |
| Glycerol stearate | 2.50% |
| Cetostearyl alcohol | 2.00% |
| Oil of paraffin | 3.00% |
| Octyldodecanol | 5.00% |
| Fraction B: | |
| Water | qsp 100.00% |
| Preservative | qs |
| Fraction C: | |
| Extract of tamarind enriched in xyloglycans | 5.00% |

The process of preparation and production of the face cream above consist essentially in heating fraction A and fraction B to 80° C., introducing fraction A into fraction B with stirring (by means of a turbine) and maintaining the mentioned temperature, cooling the mixture to 45° C. with stirring, and adding the fraction C and finally bringing the final obtained preparation to ambient temperature, with rotary stirring.

EXAMPLE 2

A cosmetic product in the form of a face gel according to the invention can, for example, have a weight composition constituted by fractions A, B, C, D and E, as indicated hereafter.

| Fraction A: | |
| --- | --- |
| Water | qsp 100.00% |
| Preservative | qs |
| Glycerine | 3.00% |
| Dimethicon copolymer | 2.00% |
| Fraction B: | |
| Xanthan gum | 0.40% |
| Fraction C: | |
| Extract of tamarind seeds enriched in xyloglycans | 10.00% |
| Fraction D: | |
| Polyacrylamide (and) C13–14 isoparaffin (and) laureth-7 | 4.00% |
| Fraction E: | |
| Perfumes | 0.40% |

The process of preparation and production of the above face gel consist essentially in preparing the fraction A at 50°

C., dispersing fraction B in fraction A with agitation (by means of a turbine), letting cool the mixture A+B to ambient temperature, adding thereto successively fraction C and fraction D whilst effecting simultaneously homogenization to obtain a homogeneous gel, adding fraction E and finally homogenizing and deaerating the final obtained product.

EXAMPLE 3

A cosmetic product in the form of a body milk according to the invention can for example have a weight composition constituted from fractions A, B, C, D, E and F as follows, as indicated hereinafter.

| Fraction A: | |
|---|---|
| Cetostearyl alcohol (and) ceteareth-20 | 1.500% |
| Glycerol stearate (and) PEG-100 stearate | 1.000% |
| Autoemulsionable propylene glycerol stearate | 2.000% |
| Paraffin oil | 4.000% |
| Isopropyl myristate | 2.000% |
| Caprylic/capric triglyceride | 6.000% |
| Fraction B: | |
| Water | qsp 100.000% |
| Propylene glycol | 2.000% |
| Preservative | qs % |
| Fraction C: | |
| Extract of tamarind seeds enriched in xyloglycans | 5.000% |
| Fraction D: | |
| Xanthan gum | 0.400% |
| Preservatives | 0.060% |
| Water | 19.540% |
| Fraction E: | |
| Magnesium aluminum silicate | 0.900% |
| Preservatives | 0.054% |
| Water | 17.049% |
| Fraction F: | |
| Perfume | 0.400% |

The process of preparation and production of the above body milk consist essentially in preparing separately fractions D and E, preparing fraction B at 80° C., adding thereto fractions D and E cooled to ambient temperature and maintaining the mixture B+D+E at 80° C. Then fraction A is prepared at 80° C., adding with agitation (by means of a turbine) said fraction A to the mixture B+D+E at 80° C., effecting cooling of the mixture A+B+D+E, adding fraction C to this latter when it is cooled to about 45° C. to 50° C., with agitation (by means of a turbine). Finally, fraction F is added when the above mixture A+B+C+D+E reaches 40° C., then the final preparation thus obtained is cooled to ambient temperature, with rotary stirring.

EXAMPLE 4

A cosmetic product in the form of treatment shampoo according to the invention can for example have a weight composition constituted of fractions A, B, C, D and E as follows, as indicated hereinafter.

| Fraction A: | |
|---|---|
| Water | qsp 100.00% |
| Preservative | qs |
| Hydroxypropyltrimonium chloride/hydroxypropyl guar gum | 0.40% |
| Fraction B: | |
| Sodium sulfate laureth (and) lauryl polyglucose | 25.00% |
| Fraction C: | |
| Cocamidopropyl betaine | 8.00% |
| Glycerol PEG 7 cocoate | 0.50% |
| Dimethicon copolyol | 1.00% |
| Perfume | 0.30% |
| Fraction D: | |
| Aqueous solution of sodium citrate | qsp Ph = 6 |
| Fraction E: | |
| Extract of tamarind seeds enriched in xyloglycans | 5.00% |

The process of preparation and production of treatment shampoo whose composition is indicated above consist essentially in preparing the fraction A at 80° C. with stirring (by means of a turbine), cooling said fraction A to ambient temperature, adding thereto successively the fractions B, C, D and E, at ambient temperature and finally filtering the mixture obtained with an 80 μm filter.

EXAMPLE 5

A cosmetic product in the form of a capillary emulsion according to the invention can for example have a weight composition constituted of fractions A, B, C, D and E as follows, as indicated hereinafter.

| Fraction A: | |
|---|---|
| Glycerol stearate (and) PEG-100 stearate | 2.50% |
| Oleic alcohol | 2.00% |
| Dimethicon | 1.00% |
| Cyclomethicon | 2.00% |
| Fraction B: | |
| Water | qsp 100.00% |
| Preservative | qs |
| Hydroxypropyltrimonium chloride guar gum | 1.00% |
| Guar gum | 1.00% |
| Fraction C: | |
| Extract of tamarind seeds enriched in xyloglycans | 5.00% |
| Fraction D: | |
| Solution of citric acid/sodium citrate | qs pH = 6 |

The process of preparation and production of the capillary emulsion described above consist essentially in preparing fraction A at 75° C., preparing separately fraction B with agitation (by means of a turbine) at 75° C., until a homogeneous structure is obtained with a complete dispersion of the gums, adding fraction A to fraction B, maintaining agitation and cooling the mixture A+B to 50° C., all the while continuing agitation. Then, fraction C is added to the above mixture A+B at 50° C., the resulting mixture A+B+C is homogenized, the latter is cooled to ambient temperature with rotary stirring and finally adjusting the pH of the mentioned mixture with the fraction D.

EXAMPLE 6

A pharmaceutical product for topical use in the form of a pomade, according to the invention, can for example have a weight composition as indicated below.

| | |
|---|---|
| Zinc oxide | 5% |
| Water | 10% |
| Lanolin | 35% |
| Vaseline | 35% |
| Extract of tamarind seeds enriched in xyloglycans | 15% |

The process of preparation and production of the pomade, whose composition is indicated above, consist essentially in melting the mixture of lanolin and vaseline at a temperature of about 60° C., incorporating the finely screened zinc oxide and finally adding the solution consisted by the mixture of water with the extract of tamarind seeds enriched in xyloglycans.

Of course, the invention is not limited to the described embodiments. Modifications remain possible, particularly as to the composition of the various elements or by the substitution of technical equivalents, without thereby departing from the scope of protection of the invention.

I claim:

1. A method of cosmetic or pharmaceutical treatment, comprising applying to a subject's skin or other exposed body parts a topical composition comprising plant extracts consisting essentially of at least 0.05% by weight of an extract of tamarind seeds, said extract having been produced by subjecting tamarind seed material to extraction with heated acidic solution, said extract comprising a mixture of xyloglycans occurring in tamarind seeds, said extract having a higher proportion of xyloglycans than occurs naturally in tamarind seeds.

2. The method according to claims 1, wherein said composition comprises said extract in an amount between 0.05% and 100% by weight.

3. The method according to claim 2, wherein said composition comprises said extract in an amount between 1% and 25% by weight.

4. The method according to claim 1, wherein said xyloglycans are present in said extract in relative proportions identical to those occurring in tamarind seeds.

5. Cosmetic product for application to skin or other exposed body parts, comprising plant extracts consisting essentially of at least 0.05% by weight of an extract of tamarind seeds in admixture with a topically acceptable carrier, said extract having been produced by subjecting tamarind seed material to extraction with heated acidic solution, said extract comprising a mixture of xyloglycans occurring in tamarind seeds, and in amounts greater than those occurring in tamarind seeds.

6. The product according to claim 5, comprising between 1% and 25% by weight of said extract, said extract comprising said xyloglycans in relative proportions identical to those occurring tamarind seeds.

7. Pharmaceutical product for application to skin or other exposed body parts, comprising plant extracts consisting essentially of at least 0.05% by weight of an extract of tamarind seeds in a mixture with a topically acceptable carrier, said extract having been produced by subjecting tamarind seed material to extraction with heated acidic solution, said extract comprising a mixture of xyloglycans occurring in tamarind seeds, and in amounts greater than those occurring in tamarind seeds.

8. The product according to claim 7, comprising between 1% and 25% by weight of said extract, said extract comprising said xyloglycans in relative proportions identical to those occurring tamarind seeds.

* * * * *